United States Patent [19]

Yamashita et al.

[11] Patent Number: 5,175,300
[45] Date of Patent: Dec. 29, 1992

[54] PROCESS FOR PREPARING PYRIDINE-2,3-DICARBOXYLIC ACID COMPOUNDS

[75] Inventors: Takaharu Yamashita; Mitsuhiro Kodama, both of Wakayama, Japan

[73] Assignee: Sugai Chemical Ind. Co., Ltd., Wakayama, Japan

[21] Appl. No.: 646,958

[22] PCT Filed: Mar. 17, 1989

[86] PCT No.: PCT/JP89/00288

§ 371 Date: Dec. 29, 1989

§ 102(e) Date: Dec. 29, 1989

[87] PCT Pub. No.: WO89/08645

PCT Pub. Date: Sep. 21, 1989

Related U.S. Application Data

[63] Continuation of Ser. No. 445,621, Dec. 29, 1989, abandoned.

[30] Foreign Application Priority Data

Mar. 18, 1988 [JP] Japan .................. 63-66772

[51] Int. Cl.$^5$ .................. C07D 213/08; C07D 69/66
[52] U.S. Cl. .................. 546/250; 560/176
[58] Field of Search .................. 546/250; 560/176

[56] References Cited

U.S. PATENT DOCUMENTS 4,723,011  2/1988  Doehwer et al. .................. 546/250
4,973,695  11/1990  Yamashita et al. .................. 213/8

FOREIGN PATENT DOCUMENTS 0220518  3/1988  European Pat. Off. .................. 213/8
0274379  6/1989  European Pat. Off. .................. 213/8

OTHER PUBLICATIONS

Journal of the American Society, vol. 7, Jan.-Apr. 1950, pp. 5221-5225; L. H. Conover et al.: "Thiazole Analogs of Pyridoxine".

Journal of the Chemical Society, vol. 438, Part III, 1949, pp. 2049-2054, the Chemical Society, London, GB; G. W. Holton et al.: "Experiments on the Synthesis of Rotenone and its Derivatives", Part XVI. The Synthesis of Abutic Acid and its Analogues: P. 2050: "Experimental Part".

Primary Examiner—Mary C. Lee
Assistant Examiner—Joseph K. McKane
Attorney, Agent, or Firm—Finnegan, Henderson, Farabow, Garrett & Dunner

[57] ABSTRACT

A process for preparing pyridine-2,3-dicarboxylic acid compounds of the following formula, which comprises preparing α-halo-oxalacetic acid diesters by reacting oxalacetic acid diester alkali metallic salts with an acid and a halogenating agent or by reacting oxalic acid diesters with halo-acetic acid esters, and then reacting the obtained α-halo-oxalacetic acid diesters with 2-propenal compounds and ammonia.

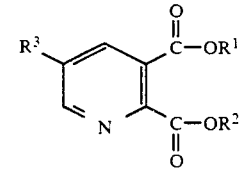

wherein $R^1$ and $R^2$ are, identical or different, a lower alkyl group, and $R^3$ is a hydrogen atom or a lower alkyl group.

The pyridine-2,3-dicarboxylic acid componds obtained by the process of the ivention are useful as an intermediate for manufacturing agricultural chemicals and pharmaceuticals.

8 Claims, No Drawings

PROCESS FOR PREPARING PYRIDINE-2,3-DICARBOXYLIC ACID COMPOUNDS

This application is a continuation of application Ser. No. 07/445,621, filed Dec. 29, 1989, now abandoned.

DESCRIPTION

1. Technical Field

This invention relates to a process for preparing pyridine-2,3-dicarboxylic acid compounds. More particularly, it relates to a process for preparing pyridine-2,3-dicarboxylic acid compounds which are useful as an intermediate for manufacturing agricultural chemicals and pharmaceuticals.

2. Background Art

Heretofore, as the method of preparing pyridine-2,3-dicarboxylic acid compounds known are:

(1) Oxidation with nitric acid of quinolines and quinolinols which are synthesized by Skraup reaction from aniline and glycerine with concentrated sulfuric acid and nitrobenzene. (J. Chem. Soc. page 4433, 1956);

(2) Reacting an α,β-unsaturated hydrazone compound and a maleic acid compound in an inert solvent to obtain 1-(substituted amino)-1,4-dihydropyridine-2,3-dicarboxylic acid derivative. Then, heating the resultant derivative to eliminate the substituted amino group in the 1-position. (Japanese Patent Application Unexamined Publication No. 246369/1985).

(3) Treating a 1-(substituted amino)-1,2,3,4-tetrahydropyridine-2,3-dicarboxylic acid derivative with acid and/or by heat to convert into a 1,4-dihydropyridine-2,3-dicarboxylic acid derivative, and then oxidizing it. (Japanese Patent Application Unexamined Publication No. 47482/1986).

(4) Oxidizing quinoline with excess hypochlorites in the presence of ruthenium oxide. (Japanese Patent Application Unexamined Publication No. 212563/1986).

(5) Condensing and cyclizing α-halo-β-keto-esters and α,β-unsaturated aldehydes or ketones in the organic solvent in the presence of more than 2 mole equivalent of ammonium salt. (Japanese Patent Application Unexamined Publication No. 106081/1987).

As the method of synthesizing pyridinemonocarboxylic acid derivatives known is such a method as subjecting ethyl 2-methly-1,4-dihydronicotinate which is produced by condensation and cyclization of α,β-unsaturated aldehydes such as acrolein and crotonaldehyde with ethyl β-aminocrotonate to oxidation with nitric acid in a mixed acid. (J. Org. Chem. Soc. Vol. 21, page 800, 1956).

However, the above method (1) not only has many reaction processes but also requires drastic oxidation with nitric acid, and involves possible hazards. Also, the pyridine-2,3-dicarboxylic acids, which are apt to cause decarboxylation, result in low yields by the oxidation with nitric acid, and, in addition, produce a large quantity of acidic waste liquid. Thus, the method (1) is not suited to the industrial manufacture of pyridine-2,3-dicarboxylic acids.

The methods (2) and (3) mentioned above have many reaction processes leading to decreased total yields, and require the use of expensive starting materials. Particularly, they require elimination process of the substituted amino group in the intermediate. This decreases the yield and becomes a problem on resource saving. Therefore, it is difficult to manufacture pyridine-2,3-dicarboxylic acid derivatives industrially by the method (2) or (3).

In the method (4), there are problems that a large excess of the oxidant must be used and that a large quantity of waste liquid is produced requiring expenses for its disposal.

In the method (5), α-halo-β-keto-ester used as a raw material cannot be produced in good yield with conventional known manufacturing methods, causing high cost of raw material. It is, therefore, difficult to manufacture pyridine-2,3-dicarboxylic acid derivatives industrially by the method (5).

Accordingly, it is an object of this invention to provide a process for preparing pyridine-2,3-dicarboxylic acid compounds in high yield from starting materials inexpensive and readily available.

DISCLOSURE OF INVENTION

A process for preparing pyridine-2,3-dicarboxylic acid compounds of the invention is a process for preparing pyridine-2,3-dicarboxylic acid compounds represented by the following formula (1).

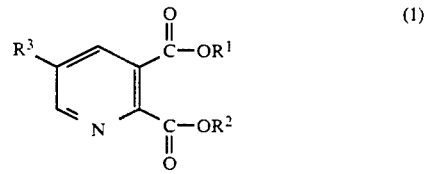

wherein $R^1$ and $R^2$ are, identical or different, a lower alkyl group, and $R^3$ is a hydrogen atom or a lower alkyl group, which comprises, 1) a compound of the following formula (2):

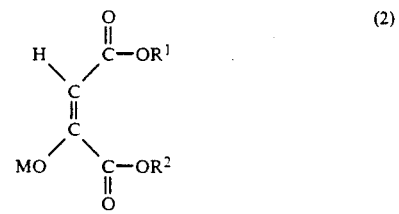

wherein $R^1$ and $R^2$ are the same as defined above and M is an alkali metal, is reacted with an acid and a halogenating agent to give a compound of the following formula (3):

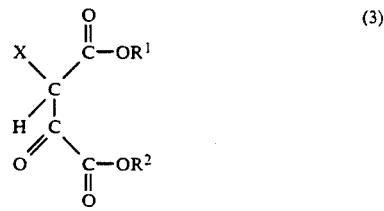

wherein $R^1$ and $R^2$ are the same as defined above and X is a halogen atom, then, the compound of the above formula (3) is reacted with the compound of the following formula (4):

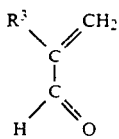

wherein R³ is the same as defined above, and ammonia, or 2) a compound of the following formula (5):

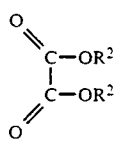

wherein R² is the same as defined above, is reacted with a compound of the following formula (6):

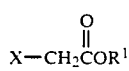

wherein R¹ and X are the same as defined above, in an aprotic solvent and in the presence of an alkali metal or a basic alkali metallic salt to give a compound of the following formula (7):

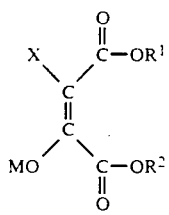

wherein R¹, R², X and M are the same as defined above, then the compound of the above formula (7) is treated with an acid to give the compound of the following formula (3):

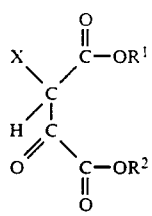

wherein R¹, R² and X are the same as defined above, then the compound of the above formula (3) and that of the following formula (4):

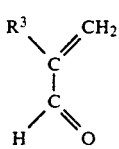

wherein R³ is the same as defined above, are reacted with ammonia.

In each formula mentioned above, examples of the lower alkyl groups for R¹, R², and R³ include, for example, straight or branched chain alkyl groups having 1 to 8 carbon atoms such as methyl, ethyl, propyl, isopropyl, butyl, isobutyl, tertiary-butyl, pentyl, hexyl, heptyl, octyl, 2-ethylhexyl group, and the like.

Examples of alkali metal for M include, for example, sodium, potassium, and the like.

Examples of the halogen atom for X include, for example, fluorine atom, chlorine atom, bromine atom, and the like.

Examples of the compound of the formula (2) include, for example, dimethyl oxalacetate sodium salt, diethyl oxalacetate sodium salt, methyl ethyl oxalacetate sodium salt, dimethyl oxalacetate potassium salt, diethyl oxalacetate potassium salt, di-tertiary-butyl oxalacetate sodium salt, di-tertiary-butyl oxalacetate potassium salt, dipropyl oxalacetate sodium salt, dipropyl oxalacetate potassium salt, and the like.

Examples of the compound of the formula (3) include, for example, dimethyl α-chlorooxalacetate, diethyl α-chlorooxalacetate, methyl ethyl α-chlorooxalacetate, dimethyl α-bromooxalacetate, diethyl α-bromooxalacetate, di-tertiary-butyl α-chlorooxalacetate, dipropyl α-chlorooxalacetate, dipropyl α-fluorooxalacetate, and the like.

Examples of the compound of the formula (4) include, for example, acrolein, 2-methyl-2-propenal, 2-ethyl-2-propenal, 2-propyl-2-propenal, 2-isopropyl-2-propenal, 2-butyl-2-propenal, 2-pentyl-2-propenal, 2-hexyl-2-propenal, 2-heptyl-2-propenal, 2-octyl-2-propenal, and the like.

Examples of the compound of the formula (5) include, for example, dimetyl oxalate, diethyl oxalate, dipropyl oxalate, diisopropyl oxalate, dibutyl oxalate, di-tertiary-butyl oxalate, dipentyl oxalate, dihexyl oxalate, diheptyl oxalate, dioctyl oxalate, and the like.

Examples of the compound of the formula (6) include, for example, methyl chloroacetate, methyl bromoacetate, methyl fluoroacetate, ethyl chloroacetate, ethyl bromoacetate, ethyl fluoroacetate, propyl chloroacetate, isopropyl chloroacetate, propyl bromoacetate, butyl chloroacetate, isobutyl chloroacetate, tertiarybutyl chloroacetate, butyl bromoacetate, hexyl chloroacetate, hexyl bromoacetate, octyl chloroacetate, and the like.

Examples of the compound of the formula (7) include, for example, dimethyl α-chlorooxalacetate sodium salt, diethyl α-chlorooxalacetate sodium salt, methyl ethyl α-chlorooxalacetate sodium salt, dimethyl α-bromooxalacetate potassium salt, diethyl α-bromooxalacetate potassium salt, di-tertiary-butyl α-chlorooxalacetate sodium salt, di-tertiary-butyl α-chlorooxalacetate potassium salt, dipropyl α-chlorooxalacetate sodium salt, dipropyl α-fluorooxalacetate potassium salt, and the like.

The preparation method of this invention can be shown with the following reaction schemes 1 and 2.

Reaction scheme 1

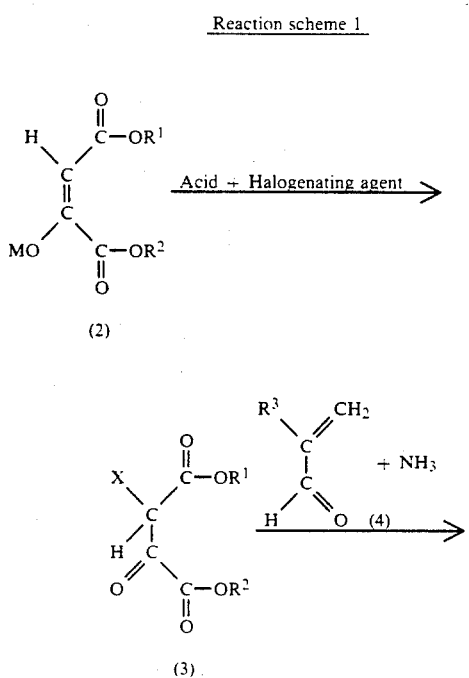

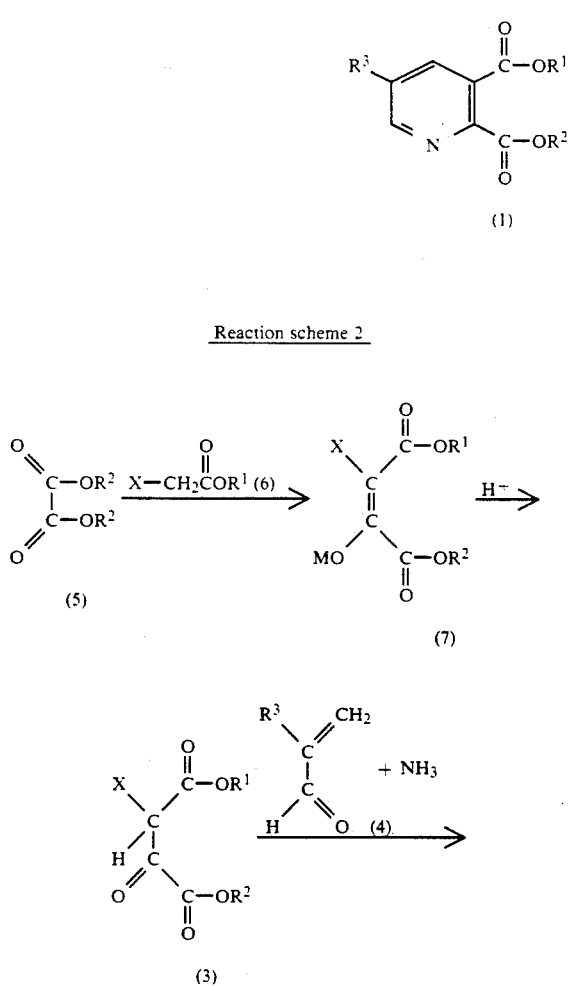

-continued
Reaction scheme 2

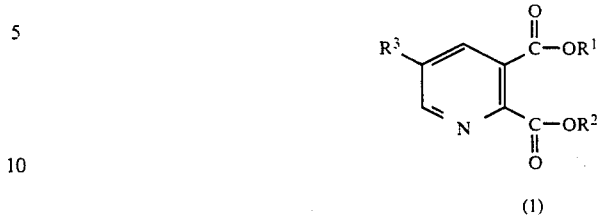

In the above formulae, $R^1$, $R^2$, $R^3$, X, and M are the same as defined before.

In the above Reaction schemes, the reaction of the reaction scheme 1 comprises a step which obtains the compound of the formula (3) by reacting the compound of the formula (2), an acid and a halogenating agent (step 1) and a step which obtains the compound of the formula (1) by reacting the compound of the formula (3) obtained above, the compound of the formula (4) and ammonia (step 2).

In the reaction of the step 1, examples of the acid used in the step include inorganic acids such as hydrochloric acid, sulfuric acid, nitric acid, and phosphoric acid, and organic acids including lower alkanoic acids such as formic acid, oxalic acid, acetic acid, and propionic acid, and sulfonic acids such as methanesulfonic acid, ethanesulfonic acid, benzenesulfonic acid, and toluenesulfonic acid. Examples of the halogenating agent include sulfuryl chloride, bromine, and chlorine.

This reaction can be carried out by either process, in which the compound of the formula (2) is allowed to react with the halogenating agent in the presence of the acid or in which the compound of the formula (2) is treated with the acid and then allowed to react with the halogenating agent.

It is desirable to carry out the reaction in an organic solvent. Any organic solvent may be used unless the solvent affects the reaction, but aprotic solvents including aromatic hydrocarbons such as toluene and benzene, and halogenated hydrocarbons such as chloroform, 1,2-dichloroethane and carbon tetrachloride are desirable.

The reaction temperature at which reaction of the compound of the formula (2) or its acid-treated compound with the halogenating agent takes place is not particularly specified, but, in general, the reaction is carried out at 0°–100° C., and preferably at 0°–50° C. The reaction is completed in 30 minutes to 10 hours, generally 1 to 5 hours.

The molar ratio of compound of the formula (2) to the halogenating agent can be varied widely, but in general it is desirable to use 0.6–1.5 mols, preferably 1–1.3 mols of the halogenating agent to 1 mol of the compound of the formula (2). The acid is used at least an equimolar amount, and preferably slightly in excess to the compound of the formula (2).

Combinations of the above-mentioned acid, organic solvent, and halogenating agent are optional, but it is most desirable to combine alkanoic acids, in particular, formic acid as acid, and halogenated hydrocarbons, in particular, chloroform as organic solvent, and sulfuryl chloride as halogenating agent.

The compound of the formula (3) which is obtained in this way can be used for the reaction of step 2 without isolation or after isolation and purification by a manner such as distillation and column chromatography.

The reaction of the step 2 is carried out to obtain the compound of the formula (1) by allowing the compound of the formula (3) obtained above to react with the compound of the formula (4) and ammonia.

The reaction is carried out under the condition free from solvent or in the organic solvent. Any organic solvent which does not affect the reaction can be used irrespective of polar, nonpolar, protic, or aprotic. Examples of solvents include alcohol such as methanol, ethanol, isopropyl alcohol, and butanol; halogenated hydrocarbons such as chloroform, 1,2-dichloroethane, and carbon tetrachloride; aromatic hydrocarbons such as benzene, toluene, xylene, chlorobenzene, o-dichlorobenzene, and nitrobenzene; ethers such as dimethyl ether, diethyl ether, dibutyl ether, tetrahydrofuran, dioxane, ethylene glycol dimethyl ether, ethylene glycol diethyl ether, diethylene glycol dimethyl ether, and dibenzyl ether; esters such as methyl acetate and ethyl acetate; aprotic polar solvents, for example, sulfoxides such as dimetyl sulfoxide, carboamides such as N,N-dimethylformamide, sulfones such as dimethyl sulfone and sulfolane, and hexamethylphosphoric triamide. The above-mentioned organic solvent can be used in a mixture of two or more types. Among them, aprotic organic solvents are desirable.

Reaction temperature is not particularly specified and the reaction can be carried out at various temperatures; for example, temperature range from 10° to 200° C.; in particular, 35°-130° C. is more desirable. It is desirable to carry out the reaction under pressure, in particular, with ammonia pressurized at 0.3-2.5 kg/cm$^2$. The reaction is completed in 30 minutes to 24 hours, in general in about 1-10 hours.

The compounds of the formulae (3) and (4) can be used at the proper molar ratio; for example, 0.8-1.5 mols, particularly 1.0-1.2 mols of the compound of the formula (4) to 1.0 mol of the compound of the formula (3) is used desirably. Ammonia is used usually in excess to the compounds of the formulae (3) and (4).

To increase the yield of the desired compound, the above-mentioned reaction is preferably carried out in the presence of ammonium salt such as ammonium carbonate, ammonium chloride, ammonium sulfate, ammonium nitrate, ammonium phosphate, and ammonium acetate.

The above-mentioned ammonium salt can be used in an adequate amount, but it is desirable to use 0.05-1.0 mol of the ammonium salt to 1 mol of the compound of the formula (4).

The preparation process described in the aforementioned reaction scheme 2 comprises a step which obtains the compound of the formula (7) by reacting the compound of the formula (5) and the compound of the formula (6) in an aprotic solvent and in the presence of an alkali metal or a basic alkali metallic salt (step 1), a step which obtains the compound of the formula (3) by treating the compound of the formula (7) prepared above with an acid (step 2), and a step which obtains the compound of the formula (1) by reacting the compound of the formula (3) prepared above, the compound of the formula (4) and ammonia (step 3).

The reaction of the above-mentioned step 1 is the reaction to condense the compounds of the formulae (5) and (6) in the aprotic solvent and in the presence of alkali metal or basic alkali metallic salt. Examples of the aprotic solvent used in the reaction include ethers such as dimethyl ether, diethyl ether, dibutyl ether, tetrahydrofuran, dioxane, ethylene glycol dimethyl ether, ethylene glycol diethyl ether, diethylene glycol dimethyl ether, and dibenzyl ether; aromatic hydrocarbons such as benzene, toluene, xylene, chlorobenzene, o-dichlorobenzene, and nitrobenzene, and the like.

Examples of alkali metal used include sodium an potassium, those of basic alkali metallic salt include alkali metallic alcoholates such as sodium methoxide, sodium ethoxide, and potassium tertiary-butoxide; alkyl alkali or aryl alkali such as methyl lithium, ethyl lithium, propyl lithium, n-butyl lithium, tertiary-butyl lithium, and phenyl lithium; alkaline metallic hydrides such as sodium hydride and potassium hydride, and the like.

The reaction usually is carried out at room temperature to elevated temperature at around 60° C. and completed in about 10 hours to 3 days, usually in about 24-48 hours.

The compounds of the formulae (5) and (6) can be used at the proper molar ratio; for example, 0.8-2.0 mols, particularly 1.0-1.5 mols of the compound of the formula (6) to 1.0 mol of the compound of the formula (5) is used desirably. Alkali metal or basic alkali metallic salt is used at least an equimolar amount, desirably in excess, to the compound of the formula (5).

The compound of the formula (7) which is obtained in this way is used for the reaction of step 2 without isolation or after isolation and purification by a manner such as washing and recrystallizing.

The reaction of the step 2 is the reaction to obtain the compound of the formula (3) by treating the compound of the formula (7) with an acid. Any acids can be used for this reaction irrespective of inorganic or organic, and the acids exemplified in the step 1 of the reaction scheme 1 can be used.

The above-mentioned acid treatment is usually carried out by allowing the excess amount of acid to act on the compound of the formula (7) in the presence of water-insoluble solvent (e.g. diethyl ether, dibutyl ether, benzene, toluene, xylene, chlorobenzene, and the like) and water, and separating the water-insoluble solvent layer.

The compound of the formula (3) which is obtained in this way is used for the reaction of step 3 without isolation or after isolation and purification by a manner such as distillation and column chromatography.

The reaction of the step 3 is the reaction to obtain the compound of the formula (1) by reacting the compound of the formula (3) obtained above, the compound of the formula (4) and ammonia.

This reaction is the the same reaction of the step 2 of the reaction scheme 1, and reaction conditions such as solvent, reaction temperature and time, and molar ratio of the compounds to be used are the the same as that of the step 2 of the reaction scheme 1.

The ester compound of the formula (1) which is obtained through the process of this invention can be converted to corresponding pyridine-2,3-dicarboxylic acid compound by hydrolysis using the known method. The hydrolysis can be carried out in water or aqueous solvent by the conventional method using basic compounds such as alkali metal hydroxides including sodium hydroxide and potassium hydroxide; alkali metal carbonates such as sodium carbonate and potassium carbonate; and alkali metal hydrogen carbonates such as sodium hydrogencarbonate and potassium hydrogencarbonate, however, alkali metal hydroxides are desirable to achieve completely the reaction. The hydrolysis is carried out at room temperature to 150° C., preferably at 40°-100° C. and completed usually in about 1-24 hours.

The desired carboxylic acid compounds can be obtained by subjecting the carboxylic acid salts produced by the above hydrolysis to acid precipitation with a mineral acid such as hydrochloric acid, sulfuric acid, nitric acid, or phosphoric acid at 20°-60° C.

In the aforementioned reaction schemes 1 and 2, the compounds of the formulae (2), (5) and (6) which are starting materials are known compounds. As the process to prepare the compound of the formula (3), the method described in J. Amer., Chem., Soc., Vol. 72, 5221, (1950) is known, but the method described therein, namely the compound of the formula (2) having ethyl group for $R^2$ and sodium for M is reacted with sulfuryl chloride or bromine in chloroform provides the object compound in the yield of as low as 31%, which is not suited to manufacturing the compound of the formula (3) in the industrial scale. According to the process of the invention, since the compound of the formula (2) is reacted with acid and halogenating agent, the compound of the formula (3) can be obtained in a high yield in contrast to the above method, resulting in improvement of the yield of the compound of the formula (1).

Industrial Applicability

Pyridine-2,3-dicarboxylic acid compounds obtained by the process of this invention is useful as the intermediate for synthesizing various compounds such as agricultural chemicals and pharmaceuticals.

The process to prepare pyridine-2,3-dicarboxylic acid compounds according to the invention can produce the pyridine-2,3-dicarboxylic acid compounds with less steps and in high yield. In particular, it has a feature to carry out the reaction without isolating the intermediate. Further, the process permits the use of inexpensive readily available starting material, can be performed in safety because the reaction proceeds under the mild conditions, and realizes easy disposal of waste liquid. Thus, the pyridine-2,3-dicarboxylic acid compounds can be manufactured in the industrial scale.

EXAMPLES

Hereinafter, the invention is described in detail with reference to Manufacturing example and Examples, but it should be understood that the invention is not limited to these examples alone.

MANUFACTURING EXAMPLE 1

In a 300-ml four-neck flask were placed 41 g of dimethylamine hydrochloride (0.502 mol) and 42.7 g of 37% formalin (0.527 mol), and 84 g of n-decylaldehyde (0.527 mol) was added dropwise thereto at 20° to 30° C. over a period of about 1 hour. After allowing to react for 6 hours at 70° to 75° C., the mixture was heated for 30 minutes at 110° C. Cooling down to room temperature, the solution was separated into oil layer and water layer. The oil layer (88 g) was distilled in vacuo, and 69 g of 2-(n-octyl)-2-propenal (bp$_{15}$: 108.5° to 110° C.) was obtained.

IR (liquid film): 2930, 2850, 1700 cm$^{-1}$.

EXAMPLE 1

In a 500-ml four-neck flask with a reflux condenser were placed 221 ml of chloroform and 13.1 g of 90% formic acid (0.26 mol), and 44.2 g of oxalacetic acid diethyl ester sodium salt (0.21 mol) was added thereto at room temperature. After stirring for 2 hours at 20° to 25° C., 41.1 g of sulfuryl chloride (0.30 mol) was added dropwise thereto at 20° to 30° C. over a period of about 2 hours, and the mixture was allowed to react for 5 hours at 40° C. After cooling the content to room temperature, it was degassed in vacuo, and the resultant inorganic salt was filtered off. The filtrate was analyzed by gas chromatography, and α-chlorooxalacetic acid diethyl ester was obtained in a yield of 78%.

Next, this filtrate and 17.7 g of 2-ethyl-2-propenal (0.21 mol) were mixed in a 100-ml glass autoclave. After closing the autoclave, the internal temperature was raised to 110° C., and ammonia gas was introduced until the ammonia partial pressure reached 0.5 to 2.5 kg/cm$^2$, and the reaction was continued for 5 hours. The content was cooled to room temperature, and the insoluble matter was filtered off. The filtrate was concentrated, and the residue was distilled, and 5-ethyl-2,3-diethoxycarbonylpyridine (bp$_2$: 151° to 152° C.) was obtained in a yield of 62.4% based on the charged oxalacetic acid diethyl ester sodium salt.

This reaction was performed by using various solvents, acids and halogenating agents. The types of solvents, acids and halogenating agents and yields of the desired compound (by gas chromatography analysis) are shown in Table 1.

TABLE 1

| Solvent | Type of acid | Type of halogenating agent | Yield of diethyl α-chlorooxalacetate (%) | Yield of 5-ethyl-2,3-diethoxycarbonyl pyridine (%) |
|---|---|---|---|---|
| Chloroform | Hydrochloric acid | Sulfuryl chloride | 54.5 | 41.4 |
| Chloroform | Acetic acid | Sulfuryl chloride | 41.7 | 30.0 |
| Methylene chloride | Formic acid | Sulfuryl chloride | 65.3 | 50.0 |
| Benzene | Formic acid | Sulfuryl chloride | 40.1 | 24.0 |
| Toluene | Formic acid | Sulfuryl chloride | 64.5 | 48.5 |
| Toluene | Formic acid | Chlorine | 46.9 | 29.0 |

The yield shows the amount based on the charged oxalacetic acid diethyl ester sodium salt.

EXAMPLE 2

In a 200-liter glass lining vessel with reflux condenser, 104 kg of chloroform, 4.7 kg of 88% formic acid (89.9 mols) and 1.4 kg of ethanol were mixed at room temperature, and 14.1 kg of oxalacetic acid diethyl ester sodium salt (67.1 mols) was added thereto at 20° to 25° C. The mixture was stirred for 2 hours at 10° to 25° C., and 11.4 kg of sulfuryl chloride (84.5 mols) was added dropwise at 10° C. to 25° C. over a period of about 2 hours. After stirring for 3 hours at 40° C., the mixture was refluxed for 2 hours at 60° C., and the gas produced by the reaction was purged out. After cooling the content to room temperature, 30 liters of water was added to dissolve the inorganic salt produced by the reaction, and the mixture was separated into chloroform layer and water layer. The separated 120.6 kg of chloroform solution was analyzed by gas chromatography, and 12.3 kg of α-chlorooxalacetic acid diethyl ester (55.2 mols) was obtained. This is a yield of 82.3% based on the charged oxalacetic acid diethyl ester sodium salt.

Next, this chloroform solution, 5.6 kg of 2-ethyl-2-propenal (66.6 mols) and 1.0 kg of ammonium acetate (13.0 mols) were mixed in a 100-liter glass autoclave. After closing it, the internal temperature was raised up to 60° C. to discharge the air in the vapor phase, and the temperature was further raised to 105° C., and ammonia gas was introduced thereto until the internal pressure reached 3.5 to 6.0 kg/cm$^2$ and the reaction was conducted for 8 hours. After cooling the content to room temperature, 16 liters of water was added to dissolve the inorganic salt produced by the reaction to separate into the chloroform layer and water layer. The separated chloroform layer was concentrated, and 17.4 kg of brown oily matter was obtained. This concentrate was distilled, and 12.0 kg of 5-ethyl-2,3-diethoxycarbonyl-pyridine (47.8 mols) was obtained. This is a yield of 71.2% based on the charged oxalacetic acid diethyl ester sodium salt, and a yield of 86.6% based on the chlorinated compound.

EXAMPLE 3

In a 300-ml four-neck flask, 130 ml of toluene, 21 g of 35% hydrochloric acid, and 40 g of water were mixed, and with vigorously stirring at 20° to 25° C. in nitrogen atmosphere, 40 g of oxalacetic acid diethyl ester sodium salt (0.19 mol) was added. After stirring for 2 hours, the solution was let stand still to be separated into toluene layer and water layer. The toluene layer was washed with 100 ml of water, and was dried overnight over anhydrous sodium sulfate, and filtered. The filtrate was kept at 10° to 20° C., and 17 g of sulfuryl chloride (0.126 mol) was added dropwise over a period of 1 hour, and the reaction was continued for 5 hours at 40° C. After cooling the content to room temperature, it was degassed in vacuo. The obtained solution was analyzed by gas chromatography, and α-chlorooxalacetic acid diethyl ester was obtained in a yield of 64% based on the charged oxalacetic acid diethyl ester sodium salt.

Next, in a 300-ml glass autoclave, the obtained solution, 8.2 g of 2-methyl-2-propenal (0.117 mol) and 1.8 g of ammonium acetate (0.023 mol) were mixed. After closing the autoclave, the internal temperature was raised up to 110° C., and ammonia gas was introduced thereto so that the internal pressure be 1.5 kg/cm$^2$ or less, and the reaction was continued for 7 hours at 105° to 110° C. After cooling the content to room temperature, the insoluble matter was filtered off. The obtained filtrate was analyzed by gas chromatography, and 5-methyl-2,3-diethoxycarbonylpyridine was obtained in a yield of 42.6% based on the charged oxalacetic acid diethyl ester sodium salt.

To this obtained solution, 50 g of water and 61.6 g of 48% sodium hydroxide aqueous solution were added, and the solution was stirred under nitrogen atmosphere for 8.5 hours at 85° to 88° C. After termination of reaction, the reaction mixture was separated into toluene layer and water layer, and the water layer was decolored with activated carbon, and was treated with 50% sulfuric acid, and white crystals of 5-methylpyridine-2,3-dicarboxylic acid (mp: 184° to 186° C.) were obtained. The recrystallized product from methanol-acetone mixed solvent had a melting point of 187° to 188.5° C. (decomposition).

Element analysis: As $C_8N_7NO_4$,

|  | C | H | N |
| --- | --- | --- | --- |
| Calc'd.: | 53.06 | 3.90 | 7.73 |
| Found: | 52.63 | 3.95 | 7.68 |
| NMR(CDCl$_3$)ppm: | 2.45 (3H, s), 8.15 (1H, s), 8.57 (1H, s) | | |

EXAMPLE 4

In a 1-liter four-neck flask, 450 ml of toluene, 65 ml of 35% hydrochloric acid and 150 ml of water were added, and the mixture was vigorously stirred in nitrogen atmosphere, while 143 g of oxalacetic acid diethyl ester sodium salt (0.68 mol) was added at room temperature. After stirring for 2 hours at 20° to 25° C., it was separated into toluene layer and water layer. The toluene layer was sequentially washed with dilute sodium hydroxide aqueous solution and water, and was dried overnight over anhydrous sodium sulfate, and was filtered. While keeping the filtrate at 10° to 20° C., 87.2 g of sulfuryl chloride (0.65 mol) was added dropwise over a period of about 2.5 hours. Afterwards, the internal temperature was raised to 45° C. to allow to react for 3 hours. The content was cooled to room temperature, and was degassed in vacuo. The obtained solution was analyzed by gas chromatography, and α-chlorooxalacetic acid diethyl ester was obtained in a yield of 65% based on the charged oxalacetic acid diethyl ester sodium salt.

Next, in a 1-liter glass autoclave, the obtained solution and 78.9 g of 2-(n-octyl)-2-propenal (0.47 mol) were mixed. After closing the autoclave, the internal temperature was raised to 110° C., and the ammonia gas was introduced thereto so that the internal pressure be 0.8 to 2.0 kg/cm$^2$, and the reaction was continued for 10 hours at 110° to 115° C. After cooling the content to room temperature, the insoluble matter was filtered off, and the filtrate was sequentially washed with 70 ml of 0.3N hydrochloric acid aqueous solution, and 50 ml of water. To this toluene solution, 107 g of 48% sodium hydroxide aqueous solution and 168 ml of water were added, and the mixture was refluxed at 85° to 87° C. for 2 hours under nitrogen atmosphere. After termination of the reaction, the mixture was diluted with 300 ml of hot water, and was separated into water layer and toluene layer. The water layer was treated with 12% hydrochloric acid aqueous solution at 70° to 80° C., and 26 g of white plate-shaped crystals of 5-(n-octyl)pyridine-2,3-dicarboxylic acid (mp: 156° to 158° C.) were obtained. When recrystallized from ethanol-water mixed solvent, the melting point was 160.5° to 162° C.

IR(KBr): 3040, 2900, 2835, 1700 - 1600, 1560 cm$^{-1}$

Element analysis: As $C_{15}N_{21}NO_4$,

|  | C | H | N |
| --- | --- | --- | --- |
| Calc'd. | 64.51 | 7.58 | 5.01 |
| Found | 64.63 | 7.52 | 5.32 |
| NMR(CDCl$_3$)ppm | 0.95 (3H, t), 1.26–3.0 (14H, m), 9.15 (1H, s), 9.20 (1H, s) | | |

EXAMPLE 5

To a 500-ml four-neck flask, 210 ml of chloroform and 14.0 g of 90% formic acid (0.274 mol) were added, and 44.2 g of oxalacetic acid diethyl ester sodium salt (0.21 mol) was added thereto at room temperature.

After stirring for 2 hours at 20° to 25° C., 40 g of bromine (0.25 mol) was added dropwise over a period of 30 minutes at 10° to 15° C., and after allowing to react for 3 hours at 30° to 40° C. and for 1 hour at 60° C., the content was cooled to room temperature, and the resultant inorganic salt was filtered off.

Next, in a 100-ml glass autoclave, the obtained filtrate, 15 g of 2-ethyl-2-propenal (0.178 mol) and 3.2 g of ammonium acetate were mixed. After closing the autoclave, the internal temperature was raised to 110° C., and ammonia gas was introduced thereto so that the internal pressure be 2.5 to 3.0 kg/cm², and the reaction was continued for 9.5 hours. After cooling the content to room temperature, the insoluble matter was filtered off, and the filtrate was analyzed by gas chromatography, and 5-ethyl-2,3-diethoxycarbonylpyridine was obtained in a yield of 30% based on the charged oxalacetic acid diethyl ester sodium salt.

EXAMPLE 6

To 100 ml of diethyl ether, 5.8 g of metal sodium (0.252 mol) and 29.5 g of dimethyl oxalate (0.250 mol) were added, and 40 g of methyl chloroacetate (0.369 mol) was added dropwise over a period of 2 hours. After allowing to react for 48 hours at 25° to 30° C., the solution was diluted with 95 g of 35% acetic acid aqueous solution to be separated into ether layer and water layer. The water layer was further extracted with 100 ml of diethyl ether. The extract was mixed with the separated ether layer, and dried over anhydrous sodium sulfate. After distilling off diethyl ether, the residue was distilled in vacuo, and 22 g of dimethyl α-chlorooxalacetate (bp₈: 122° C.) was obtained (yield 45.2%).

Next, in a 500-ml glass autoclave, 120 ml of toluene, 6.5 g of 2-ethyl-2-propenal (0.077 mol) and 10 g of the obtained dimethyl α-chlorooxalacetate (0.051 mol) were charged. After the internal temperature was raised to 90° C., bubbling of ammonia gas was started at ammonia pressure of 0.5 kg/cm², and the reaction was continued for 9 hours at 105° C. The content was cooled to room temperature, and the insoluble matter was filtered off. The filtrate was dried over anhydrous sodium sulfate, and the toluene was distilled off. The residue was distilled, and 6.6 g of 5-ethyl-2,3-dimethoxycarbonylpyridine (bp₄: 158.5° to 161° C.) was obtained (yield 58.0%).

IR (liquid film): 2950, 2850, 1740, 1720 cm⁻¹
Mass spectrometry: M⁺ = 223

EXAMPLE 7

To 250 ml of toluene, 5.8 g of metal sodium (0.252 mol) and 29.5 g of dimethyl oxalate (0.250 mol) were added, and 40 g of methyl chloroacetate (0.369 mol) was added dropwise at room temperature over a period of 1 hour. The reaction was continued for 48 hours at 45° to 55° C. To the reaction mixture, 60 ml of water and 35 g of 35% hydrochloric acid were added, and the mixture was separated into toluene layer and water layer. The toluene layer was dried over anhydrous sodium sulfate, and sodium sulfate was filtered off. This filtrate and 13.2 g of 2-ethyl-2-propenal (0.157 mol) were put in a 500 ml glass autoclave. After the internal temperature was raised to 90° C., bubbling of ammonia gas was started at ammonia pressure of 0.5 kg/cm², and the reaction was continued for 4 hours at 105° C. The content was cooled to room temperature, the insoluble matter was filtered off. The filtrate was analyzed by gas chromatography, and 5-ethyl-2,3-dimethoxycarbonylpyridine was obtained in a yield of 30.6% based on the charged dimethyl oxalate.

EXAMPLE 8

To 250 ml of dibutyl ether, 5.8 g of metal sodium (0.252 mol) and 11.6 g of absolute ethanol (0.252 mol) were added, and the mixture was stirred for 1 hour. To the mixture, 36.8 g of diethyl oxalate (0.252 mol) and 33.0 g of ethyl chloroacetate (0.269 mol) were added dropwise at 30° to 35° C. over a period of 1 hour. After the continuing the reaction for 38 hours at room temperature, 80 ml of water and 35 g of 35% hydrochloric acid were added to separate the solution into ether layer and water layer. The ether layer was dried over anhydrous sodium sulfate, and sodium sulfate was filtered off. This filtrate and 21.2 g of 2-ethyl-2-propenal (0.252 mol) were charged in a 500-m) glass autoclave. After the internal temperature was raised to 90° C., bubbling of ammonia gas was started at ammonia pressure of 0.5 kg/cm², and the reaction was continued for 4 hours at 105° C. The content was cooled to room temperature, and the insoluble matter was filtered off. The filtrate was analyzed by gas chromatography, and 5-ethyl-2,3-diethoxycarbonylpyridine was obtained in a yield of 46.6% based on the charged diethyl oxalate.

We claim:

1. A process for preparing pyridine-2,3-dicarboxylic acid compounds of the formula (1);

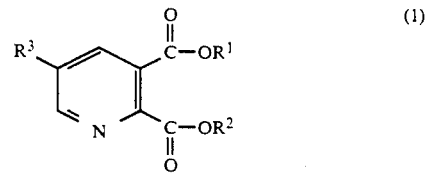

wherein $R^1$ and $R^2$ are, identical or different, each a lower alkyl group, and $R^3$ is a hydrogen atom or a lower alkyl group, which comprises, reacting a compound of the formula (2):

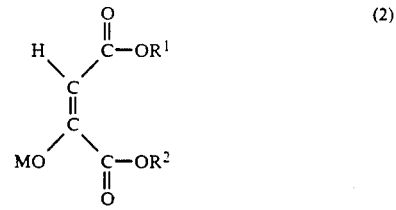

wherein $R^1$ and $R^2$ are the same as defined above and M is an alkali metal, with an acid and a halogenating agent to give a compound of the formula (3):

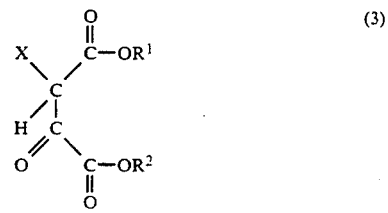

wherein $R^1$ and $R^2$ are the same as defined above and X is a halogen atom, and then, reacting the compound of formula (3) with a compound of the formula (4):

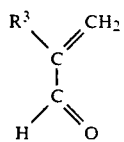 (4)

wherein $R^3$ is the same as defined above, and ammonia.

2. The process of claim 1, in which the compound of the formula (3) resulting from the reaction of the compound of formula (2) with an acid and a halogenating agent, is reacted without isolation with the compound of formula (4) and ammonia.

3. The process of claim 2, in which the reaction of the compound of formula (2) with a halogenating agent and an acid is carried out in an aprotic organic solvent at a temperature of from 0°–100° C.

4. The process of claim 3, in which the aprotic organic solvent is chloroform, the acid is formic acid, and the halogenating agent is sulfuryl chloride.

5. The process of claim 4, in which the reaction of the compounds of formulae (3) and (4) and ammonia is carried out under pressure and at temperature of from 10°–200° C.

6. The process of claim 5, in which the reaction of the compounds of the formulae (3) and (4) and ammonia is carried out in the presence of an ammonium salt.

7. The process of claim 1, in which the acid is selected from the group consisting of hydrochloric acid, sulfuric acid, nitric acid, phorphoric acid, formic acid, oxalic acid, acetic acid and propionic acid.

8. The process of claim 7, wherein the acid is formic acid.

* * * * *